United States Patent [19]

Marshall et al.

[11] Patent Number: 5,449,514
[45] Date of Patent: Sep. 12, 1995

[54] BAIT BLOCK

[75] Inventors: Edward F. Marshall, Fredonia; Peter C. Anderson, Grafton, both of Wis.

[73] Assignee: Liphatech, Inc., Milwaukee, Wis.

[21] Appl. No.: 580,761

[22] Filed: Sep. 11, 1990

[51] Int. Cl.⁶ .............................................. A01N 25/00
[52] U.S. Cl. ....................................... 424/84; 424/410
[58] Field of Search ............................................ 424/84

[56] References Cited

U.S. PATENT DOCUMENTS

| | | | |
|---|---|---|---|
| 2,813,058 | 11/1957 | Smith | 167/46 |
| 3,574,234 | 4/1971 | Boschetti et al. | 260/343.2 |
| 3,651,091 | 3/1972 | Boschetti et al. | 260/343.2 |
| 4,585,786 | 4/1986 | Berthelon | 514/432 |
| 4,891,218 | 1/1990 | Sherman | 424/84 |
| 4,950,482 | 8/1990 | Corey | 424/405 |

FOREIGN PATENT DOCUMENTS

| | | | |
|---|---|---|---|
| 2382854 | 6/1978 | France | A01N 25/00 |
| 0654980 | 3/1986 | Switzerland | A01N 43/16 |

OTHER PUBLICATIONS

Merck Index 10th Ed, 1980.

*Primary Examiner*—Marianne M. Cintins
*Assistant Examiner*—Russell Travers
*Attorney, Agent, or Firm*—Foley & Lardner

[57] ABSTRACT

A rodenticide bait block has a keyhole-shaped groove which can be formed by extrusion. A fastener, such as a nail, can be passed through the enlarged inner end of the groove and used to fasten the bait block to a surface. Various configurations are used for the external surface of the bait block to provide additional biting edges.

10 Claims, 1 Drawing Sheet

BAIT BLOCK

TECHNICAL FIELD

The present invention relates generally to pesticidal baits, more particularly to a rodenticide bait block containing a rodenticide and a feed which induces a rodent to eat the bait block.

BACKGROUND OF THE INVENTION

Rodents have been exterminated by poisoned baits for many years. Such baits have taken the form of rodenticide-impregnated grains and other foods formed into small pellets or paraffinized blocks of various sizes. The blocks or pellets are usually placed on the ground, where rodents, having mistaken their find as serendipity, would consume the poisoned food.

Scattering pellets or blocks on the ground is problematic since animals other than the target rodents can eat the poisoned food. Additionally, the bait is easily scattered or carried away. Using larger paraffinized blocks can help prevent scattering. Such blocks are provided with external ridges to provide a better biting surface for the rodent, as shown in Sherman, U.S. Pat. No. 4,891,218, issued Jan. 2, 1990, which also shows a series of small holes running through the block to provide additional biting surface as the outside of the block is eaten await.

The Sherman patent further illustrates a recess provided on the underside of the block for mounting the block on an upright peg to prevent the rodent from carrying the block away. When used in elevated locations, such as rafters, trees or fences, it is also well known to nail the block in place in a vertical or horizontal position. This can aid in keeping it out of reach of non-target animals.

Bait blocks of this type have been made by molding a mixture containing the rodenticide, the feed, and the binder (e.g. wax). Extrusion has also been used to make such products, as mentioned in Smith, U.S. Pat. No. 2,813,058, issued Nov. 12, 1957. However, when bait blocks are formed by extrusion, it is difficult to produce blocks with internal holes. Extrusion using a single orifice die cannot produce a product having an internal hole or recess. Such a hole or recess could be formed or drilled in a separate step after extrusion, but this would be inefficient and waste product. Molding the bait block makes it easier to form holes or recesses, but is slower and tends to waste more material than extrusion. Thus, there remains a need for a bait block configuration which has an internal hole to facilitate mounting and can be made by a simple extrusion process.

SUMMARY OF THE INVENTION

The present invention provides a bait block having an outwardly opening, keyhole-shaped groove which permits the block to be mounted on a peg, nailed to a surface, or wired, and also permits the block to be manufactured by extrusion wherein the block and groove are formed simultaneously.

BRIEF DESCRIPTION OF THE DRAWINGS

A preferred exemplary embodiment of the invention will be described in conjunction with the appended drawing, wherein like numerals denote like elements, and.

DETAILED DESCRIPTION OF PREFERRED EXEMPLARY EMBODIMENTS

Figure 1:
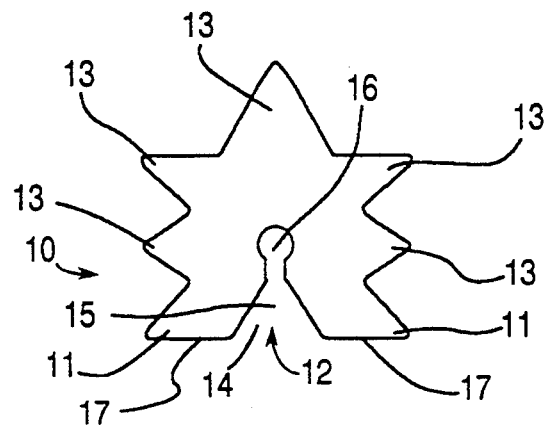
FIG. 1 is a front end view of a bait block of the invention.

Referring to FIG. 1, a bait block 10 in accordance with the invention comprises a pair of symmetrical feet 11, a keyhole-shaped lengthwise groove 12, and a series of external ridges 13. Block 10 has a uniform cross-sectional shape along its length, such that a rear end view of block 10 is identical to the front view shown in FIG. 1. Ridges 13 provide additional biting edges for the block in a manner generally known in the art.

Keyhole groove 12 has a flared outer end 14, a narrow neck 15, and an enlarged diameter inner end 16. Flared outer end 14 is located between feet 11 and tapers upwardly and inwardly to neck 15. Neck 15 is a narrow, generally planar space extending vertically between flared outer end 14 and inner end 16. Enlarged inner end 16 is preferably circular in shape to match a peg or nail. Neck 15 is narrower than the diameter of enlarged circular inner end 16 to prevent bait block 10 from falling off its fastener. For example, when a nail is inserted through one end of inner end 16 and used to fasten bait block 10 to a surface, neck 15 is narrow enough to prevent bait block 10 from sliding off the nail. For purposes of the invention, the term "keyhole-shaped groove" thus refers to a groove having a cross-sectional shape which includes a narrow outer portion (e.g. neck 15) extending outwardly from a wider inner end portion (inner end 16).

Projections 13 each have a generally triangular shape and diverge from the sides and top of the block. Feet 11 provide a pair of coplanar flat base surfaces 17 which allow block 10 to rest stably on a flat surface, if desired.

In accordance with a preferred embodiment, bait block 10 is from 2 to 8 cm long, especially about 2 to 4 cm long, so that a conventional nail can be used to mount block 10. Otherwise, the dimensions of the block can be selected as needed. Typical blocks are from 1–5 cm high and wide.

Figure 2:
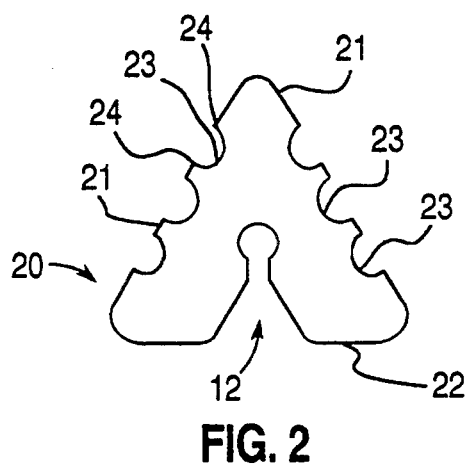
FIGS. 2 and 3 are front end views of alternative embodiments of bait blocks according to the invention.

Referring now to FIG. 2, an alternative preferred embodiment of a bait block 20 is of a generally triangular shape having a pair of sloped upper faces 21 and a lower supporting face 22. Bait block 20 has a keyhole shaped groove 12 identical to that of block 10 located in the center of bottom face 22. However, instead of projections 13, faces 21 of block 20 have each have a series of shallow, spaced, lengthwise grooves 23. In the embodiment shown, grooves 23 are concave, preferably semi-circular in cross-section. This embodiment is advantageous in that grooves 23 provide additional obtusely-angled corners 24 for biting without ridges or projections which can break off during shipment or handling.

Figure 3:
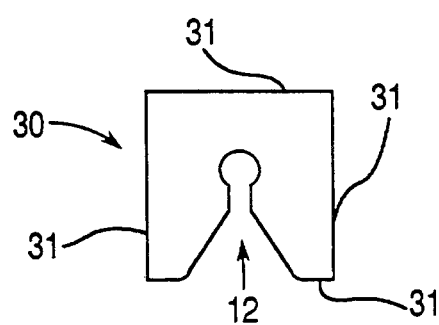

In FIG. 3, a further embodiment of a bait block 30 is of a generally polygonal, e.g., rectangular or square in cross-section. Bait block 30 has keyhole groove 12 in one of four otherwise identical flat outer faces 31.

A bait block 10, 20 or 30 in accordance with a preferred embodiment is made from a mixture of feed (i.e., grains, corn meal, seeds, or the like), combined with effective amounts of an odorous attractant, a binder such as wax, and the rodenticide. Sweeteners and flavorings can also be added. The binder is added to give the bait block strength and weatherability so that it can be used in outdoor applications. Such formulations are generally known in the art.

A preferred formulation according to the invention has been found to provide bait blocks which are extrudable, palatable to rodents, efficacious, and of good strength and weatherability. Such a formulation includes 20 to 30 wt. %, especially 20 to 25 wt. %, of whole grain seeds, e.g., millet, canary or sunflower seeds, 25 to 35 wt. % of a grain meal, such as wheat or corn meal, 5 to 15 wt. % of a leguminous meal, such as bean, clover, alfalfa, peanut, or soybean meal, 5 to 15 wt. % of a flour, such as wheat or corn flour, 25 to 35 wt. % of the binder, such as paraffin, and an effective amount, typically 0.0025 to 0.025 wt % of the rodenticide, optionally with up to about 5 wt. % of a flavoring or sweetening agent such as sugar, aspartame, saccharin or the like.

A variety of rodenticides can be used, including warfarin, pindone, isovaleryl-indandione, brodifacoum, diphacinone, chlorophacinone, bromethlin, cholecalciferol, ergocalciferol, zinc phosphide, difethialone, and bromadiolone. Bromadiolone is described in Boschetti, et al., U.S. Pat. Nos. 3,651,091, issued Mar. 21, 1972, and 3,574,234, issued Apr. 6, 1971, and marketed by Lipha Chemicals, Inc. under the trademark MAKI. Difethialone is described in Berthelon U.S. Pat. No. 4,585,786, issued Apr. 29, 1986.

Bait blocks according to the invention are preferably made by mixing the ingredients and then forming the bait blocks by extrusion. A blender first blends the ingredients to form a uniform mixture, which is then transferred by a screw conveyor to a heated barrel. The ingredients are heated to a temperature of approximately 200° F. (93.3° C.) so that the mixture becomes homogenous. This homogenous mixture is then extruded through a heated die. The die is heated to a somewhat lower temperature, such as about 140° F. (60° C.), to create back pressure which promotes more uniform extrusion.

A single blade cutter slices the extruded mixture into appropriately sized bait blocks as the mixture emerges from the die. The cutter stroke is timed according to the speed of the extrusion process so that the bait blocks are cut in predetermined lengths.

A bait block according to the invention can be secured to a mounting surface, for example, a tree, fence, wall, rafter, etc., by a variety of means. A nail or similar fastener can be inserted entirely through the inner end 16 of slot 12, so that the block can be nailed directly to a vertical or horizontal surface. The block can also be readily secured with a suitable cord, e.g. a rope or wire, which is wound around the block through inner end 16 and then tied to a suitable support, such as a post or sewer grate. Since groove 12 opens outwardly, there is no need to thread the cord through a hole. In the alternative, the block can simply be placed on its flat bottom face, for example, by means of feet 11.

It will be understood that the above description is of preferred exemplary embodiments of the invention, and that the invention is not limited to the specific forms shown. For example, the bait block can be of various dimensions and have various external ridges or projections, and can be made for use with target species other than rodents. The bait block of the invention could also be used for non-pesticidal purposes, such as for delivering a bioactive ingredient, e.g. a nutrient or medicine, to the target animal. Various other substitutions, modifications, changes, and omissions may be made in the design and arrangement of the elements without departing from the spirit of the invention as expressed in the appended claims.

We claim:

1. In a rodenticidal bait block of the type containing a binder, a rodent feed, and a rodenticidally effective amount of a rodenticide, the improvement which comprises:

said bait block having a uniform, generally polygonal cross-sectional shape along its length, a plurality of flat external side faces, and a lengthwise, outwardly-opening, keyhole-shaped groove having a uniform cross-sectional shape along its length which opens on one of the flat faces, which groove has a narrow neck which extends outwardly from a widened inner end, the widened inner end of the keyhole-shaped groove comprising a hole extending lengthwise from one end of the block to the other, and the narrow neck comprising a space formed by a pair of slightly spaced-apart inner walls of the block, which neck extends outwardly from the hole, the width of the neck being less than the width of the hole, such that the keyhole-shaped groove is suitably configured for disposing a fastener lengthwise through the widened inner end of the keyhole-shaped groove and securing the block to a mounting surface with the fastener.

2. The bait block of claim 1, wherein the block further comprises a plurality of lengthwise external ridges of uniform cross-section.

3. The bait block of claim 2, wherein the external ridges extend from the top and sides of the block, and the keyhole-shaped groove opens on a bottom face of the block.

4. The bait block of claim 1, wherein the shallow grooves are of concave shape.

5. The bait block of claim 1, wherein the block has a pair of feet having coplanar support surfaces on opposite sides of the keyhole-shaped groove.

6. The bait block of claim 1, wherein the bait block consists essentially of 20 to 30 wt. % whole grain seeds, 25 to 35 wt. % of a grain meal, 5 to 15 wt. % of a leguminous meal, 5 to 15 wt % of a flour, 25 to 35 wt. % of a wax binder, and up to about 5 wt. % of a sweetener.

7. The bait block of claim 6, wherein said seeds are selected from millet, canary, and sunflower seeds, said grain meal is wheat or corn meal, said leguminous meal is selected from bean, clover, alfalfa, peanut, or soybean meal, and said binder is paraffin.

8. The bait block of claim 7, wherein said rodenticide is present in the amount of 0.0025 to 0.025 wt. %.

9. The bait block of claim 1, wherein the widened inner end of the keyhole-shaped groove comprises a generally circular hole, and the narrow neck comprises a generally planar space formed by a pair of parallel, slightly spaced-apart inner walls of the block.

10. The bait block of claim 9, wherein the keyhole-shaped groove further comprises a flared outer end at which the spaced inner walls defining the narrow neck diverge from each other.

* * * * *